United States Patent [19]

Canzoneri et al.

[11] 4,449,101
[45] May 15, 1984

[54] JET WASH FOR ULTRASONIC STREAMING CURRENT DETECTOR

[75] Inventors: Anthony S. Canzoneri, Kenner; Joseph V. McDonald, Metairie, both of La.

[73] Assignee: Process Development, Inc., Kenner, La.

[21] Appl. No.: 435,903

[22] Filed: Oct. 22, 1982

Related U.S. Application Data

[63] Continuation-in-part of Ser. No. 375,577, May 6, 1982, Pat. No. 4,446,435.

[51] Int. Cl.³ ............................................. G01N 27/60
[52] U.S. Cl. ..................................... 324/453; 324/438
[58] Field of Search .................... 134/1; 324/439, 444, 324/446, 447, 450, 452, 453; 204/280

[56] References Cited

U.S. PATENT DOCUMENTS 3,368,145 2/1968 Gerdes ................................. 324/453
4,329,649 5/1982 Scoates ................................ 324/438

Primary Examiner—Michael J. Tokar
Attorney, Agent, or Firm—Keaty & Keaty

[57] ABSTRACT

An ultrasonic streaming current detector for developing, on a continuous basis, an electric signal which is a function of the charge condition existing in a stream containing charged particles. The present invention has a cross shaped housing having a cross member and a longitudinal member containing a pump chamber having a reciprocating piston on a pair of signal generating electrodes. A fluid injection connection is provided to the base of the longtudinal member. The piston pumps a sample stream within the pump chamber, creating a reciprocating shear force against the sample stream, generating an electric signal across the electrodes. The generated signal is representative of the average electric charge of the suspended particles in the sample stream to prevent buildup of sample particles in the pump chamber, which would bias the signal, a periodic wash backflow of a fluid is injected into the pump chamber, preferably at a point opposite the point of sample fluid injection. This jet wash purges the pump chambers, maintaining the accuracy of the sample stream.

11 Claims, 1 Drawing Figure

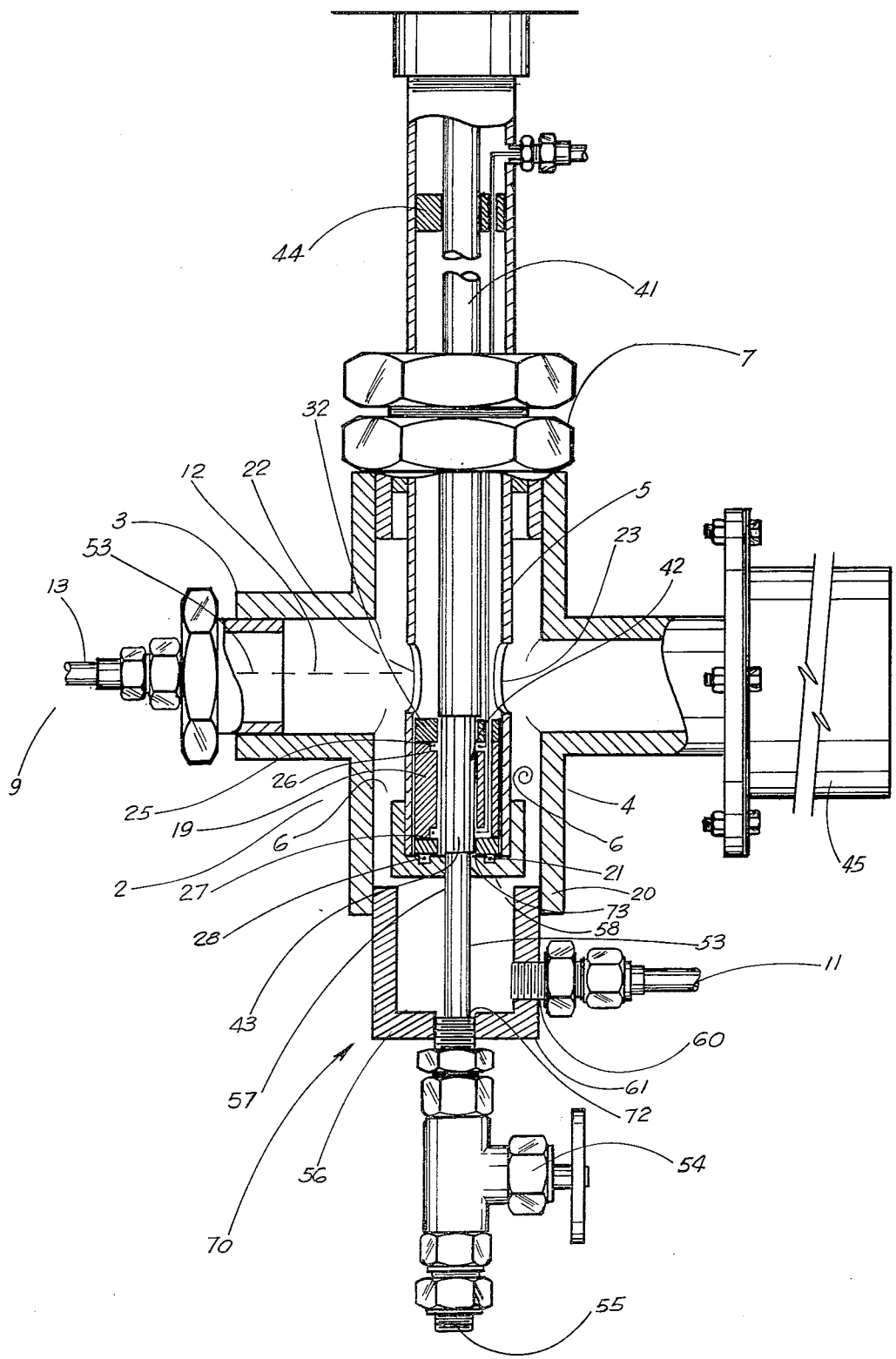

JET WASH FOR ULTRASONIC STREAMING CURRENT DETECTOR

This application is a continuation-in-part of co-pending application Ser. No. 375,577, filed May 6, 1982 now U.S. Pat. No. 4,446,435.

BACKGROUND OF THE INVENTION

The present invention teaches a supplemental or optional improvement to the ultrasonic streaming current detector apparatus of co-pending application, Ser. No. 375,577. Particularly, the present invention features a passageway means for inducing intermittently a suitable cleaning fluid, such as deionized or distilled water, or sodium hypochlorite, through a cleaning fluid inlet provided in serial combination with an adjustable valve provided in fluid communication with the bottom of a connector receptacle, which is in turn connected in fluid communication with the longitudinal element 4 of cross-shaped member 2, reference being had to said co-pending application, said passageway means ultimately fluidly communicating with a bore provided in the bottom surface of dielectric cap 20 for thereby facilitating the injection of said cleaning fluid forcibly against piston 42 and lands 43 thereof, and dielectric sleeve 19, inter alia. The setting of said adjustable valve connected in series to said cleaning fluid inlet will determine the force with which said cleaning fluid will be injected against piston 42 and lands 43 thereof, and ultra-dielectric sleeve 19, inter alia. The setting selected should allow said cleaning fluid to be injected with a force sufficient enough to cause any material, especially material containing charge-influencing species, that may have accumulated on lands 43 of piston 42 and/or in the cavity formed by piston 42, the bottom of sleeve 19 and dielectric cap 20 to be forced out between piston 42 and sleeve 19 and expelled through apertures 22, 23 into reservoir 12 and thence through egress means 13. It is important to understand that the jet wash apparatus of the present invention may be employed in addition to or in lieu of the ultrasonic cleaning device 45 of the ultrasonic streaming current detector of said co-pending application, for preventing the accumulation of any material, especially material containing charge-influencing species on or around piston 42 or dielectric cap 20. It has been discovered through experience that the readings generated by the ultrasonic streaming current detector have been inaccurate when the test fluid accumulated impurities and its concentration and make-up drastically changed. This situation has only been found to occur in extremely harsh applications of the present invention. The only applications in which the ultrasonic streaming current detector failed were when the test fluid was simulated white water and tray water as found in a paper making machine, or river water. In these situations, depending on the nature of the liquid being sampled, the jet wash apparatus of the present invention has been utilized with success, either independently, or in conjunction with the ultrasonic cleaning device 45 of the ultrasonic streaming current detector of said co-pending application.

The jet wash can be intermittently controlled manually or automatically to induce the cleaning action as indicated, particularly when the instrument can not be set to zero as a result of impurities in the chamber.

Other objects and advantages of the present invention will become apparent from the following detailed description, when read in conjunction with the following drawing, wherein:

BRIEF DESCRIPTION OF THE DRAWINGS

FIG. 1 is a cross-sectional, elevational view of the cross-shaped member of the ultrasonic streaming current detector of co-pending application, Ser. No. 375,577, with the jet wash apparatus of the present invention therein employed.

DETAILED DESCRIPTION OF THE PREFERRED EMBODIMENT

The following brief recapitulation of the ultrasonic streaming current detector of co-pending application, Ser. No. 375,577, should provide sufficient basis for the following description of the present invention, which is basically an improvement thereof, wherein:

In summary (refer now to said co-pending application), the reciprocating movement of piston 42 within the bore of dielectric sleeve 19 creates a reciprocating shear force which causes an electron flow within the streaming flow of sample fluid 9 and it is this electron flow which is detected by electrodes 25, 27, thus generating an electrical signal which is fed, into the circuitry 51 inside of meter/recorder device 36 and which is processed by this circuitry 51 to indicate the average charge density existing in the flow stream of sample fluid 9. Typical sample streams may be raw water, sewage, a latex, oil-water emulsions, or simpler water filtration systems. One of the major advantages of the ultrasonic streaming current detector of said co-pending application is the provision of an ultrasonic cleaning device 45 which continuously generates ultrasonic shock waves, or mechanical vibrations which prevent any particles, at least some of which may be charged, from agglomerating onto the walls of piston 42 or the bore of dielectric sleeve 19, but which rather causes the particles to stay suspended in the sample stream fluid 9. The elimination of agglomeration of the charged particles ensures that all electrical current generated across electrodes 25, 27 and sent via lead wires 30, 31 to circuitry 51 will be accurately representative of the charged condition of the sample stream 9, rather than being altered by the charged condition of agglomerated particles which have built up on piston 42 or the bore of dielectric sleeve 19. Because of the accurate detection of the electrical current by electrodes 25, 27, the ultimate display on the readout device (not shown) will always be accurate. However, experiments have shown that the ultrasonic cleaning device 45 of the ultrasonic streaming current detector of said co-pending application has proven somewhat ineffective in extremely harsh applications of the apparatus. Particularly, in the instances wherein simulated white water and tray water as found in a paper making machine was tested, and on tests with river water, as the simulated white water and tray water was being circulated, it accumulated impurities and its concentration and make-up changed, thereby resulting in inaccurate readings due to the accumulated impurities being detected by electrodes 25, 27. In these rare, harsh applications, it has been found that the jet wash apparatus of the present invention, indicated generally by the numeral 70 in FIG. 1, has proven extremely effective in eliminating any material that may have accumulated in the cavity formed by piston 42, the bottom of sleeve 19 and dielectric cap 20, in the manner hereinafter described. It should be noted that the jet wash apparatus of the present invention, indicated generally by the numeral 70, in FIG. 1, is an additional method of cleaning which may be used independently of or in conjunction with the ultrasonic cleaning device 45 of said co-pending application, Ser. No. 375,577.

Jet wash apparatus 70, as seen in FIG. 1, comprises a connector receptacle 56, of generally cylindrical shape, threadedly connected, preferably, to the bottom of longitudinal element 4 of cross-shaped member 2; a cleaning fluid inlet 55, preferably threadedly connected to the bottom of connector receptacle 56, for facilitating the introduction of cleaning fluid (hereinafter described) therethrough, the flow rate of said cleaning fluid being regulated by adjustable valve 54 serially connected to cleaning fluid inlet 55; a conduit 53, preferably made of polethylene, or some other suitable dielectric material, fluidly connected on its outer end 72 to cleaning fluid inlet 55, and on its inner end 73 to a bore 57 provided through the bottom surface 58 of dielectric cap 20, for thereby conveying said cleaning fluid (hereinafter described) from said cleaning fluid inlet 55 through dielectric cap 20 and into the cavity formed by piston 42, the bottom of sleeve 19 and dielectric cap 20, for reasons which will hereinafter become obvious; and a transverse bore 60 provided through one side 61 of connector receptacle 56, wherein test fluid inlet pipe 11 is connected in fluid communication therewith, for thereby facilitating the injection of said fluid to be tested through the passageway 6 formed between metal tube 5 and longitudinal element 4 of cross-shaped member 2, for facilitating testing thereof.

In operation, jet wash apparatus 70 of the present invention works in the following simple manner:

1. A jet stream of cleaning fluid, which can be deionized or distilled water, or sodium hypochlorite, for example, is injected by any suitable means (not shown), through cleaning fluid inlet 55, the flow rate thereof being controlled by means of adjustable valve 54, and thence through conduit 53 and through bore 57 provided through the bottom surface 58 of dielectric cap 20, and therethrough into the cavity formed by piston 42, the bottom of sleeve 19, and dielectric cap 20, thereby forcing any material, especially material containing charge-influencing species, that may have accumulated in this cavity, out between piston 42 and sleeve 19 and expelled through apertures 22, 23 into reservoir 12 and thence through egress means 13, thereby ensuring that electrodes 25, 27 detect only those charge-influencing species contained by the test fluid 9 which is delivered through test fluid inlet pipe 11 for testing thereof in the manner described in co-pending application, Ser. No. 375,577, thereby ultimately ensuring accurate readings by said ultrasonic streaming current detector;

2. It is important to note that the injection of said cleaning fluid through cleaning fluid inlet 55 is generally intermittent, as even in the harshest of applications of said ultrasonic streaming current detector, there are substantial lapses of time between accumulations of the charge-influencing species within the cavity formed by piston 42, the bottom of sleeve 19, and dielectric cap 20, thereby necessitating the application of the jet wash apparatus 70 of the present invention intermittently at each point in time at which these accumulations of charge-influencing species occurs;

3. Depending on the nature of the liquid being sampled, the jet wash apparatus 70 of the present invention may be used independently or in conjunction with ultrasonic cleaning device 45 of the ultrasonic streaming current detector of said co-pending application.

The foregoing description and drawing will suggest other embodiments and variations to those skilled in the art, all of which are intended to be included in the spirit of the invention as herein set forth.

What is claimed as invention is:

1. A jet wash apparatus for ultrasonic streaming current detector, having passageway means for variably conveying a cleaning fluid into said ultrasonic streaming current detector, said ultrasonic streaming current detector comprising:

a. a cross-shaped tubular member having cross-member and longitudinal elements communicating with each other and filled with a test fluid containing charge-influencing species;

b. a piston receiving member mounted coaxially with said longitudinal element;

c. a casing substantially surrounding said piston receiving member;

d. a pair of electrodes, the first of which is disposed adjacent to a bottom end of said piston receiving member and the second of which is disposed in said piston receiving member above the first electrode;

e. a reciprocating element mounted in a central bore of said piston receiving member;

f. means for reciprocating and reciprocating element within the bore of said piston receiving member, so as to cause a continuous repititive flow of said test fluid to and from said bore to thereby generate electrical signals across said electrodes;

g. means for amplifying said electrical signals generated across said electrodes and means for utilizing said amplified signals;

h. means for conducting said electrical signals generated across said electrodes from said electrodes to said means for amplifying said electrical signals and said means for utilizing said amplified signals;

i. means for synchronizing said conduction of said electrical signals with the action of said reciprocating element;

j. an ultrasonic cleaning device disposed adjacent to said piston receiving member and said casing for generating mechanical vibrations to prevent an agglomeration of said charge-influencing species contained by said test fluid in the area about said electrodes, and wherein said jet wash apparatus comprises:

a connector receptacle connected in fluid communication with the bottom of said longitudinal element of said cross-shaped tubular member;

a cleaning fluid inlet means connected in fluid communication to the bottom of said connector receptacle, said cleaning fluid inlet means having an adjustable valve;

a conduit connected in fluid communication at its bottom end to said cleaning fluid inlet means and fluidly communicating with said piston receiving member at its top end.

2. The apparatus of claim 1, wherein said longitudinal element of said cross-shaped member is provided at the slower end with ingress means for allowing intake of said test fluid which contains charge-influencing species into said longitudinal element and wherein said cross-member element of said cross-shaped member is provided at one end with egree means for allowing the outflow of said fluid from said cross-member element.

3. The apparatus of claim 2, wherein a cylindrical, dielectric cap is coupled to the bottom of said casing, thereby fluidly sealing the bore of said piston receiving member and said casing.

4. The apparatus of claim 3, wherein a chamber is formed between the outer surface of said piston receiving member and the inner surface of said longitudinal element for allowing the flow of said test fluid therethrough into a reservoir of said crossmember element.

5. The apparatus of claim 4, wherein said casing is provided with two apertures diametrically opposite each other through the walls of said casing at a point substantially coincidental with the longitudinal axis of said cross-member element, thereby providing a substantially linear fluid flow passage through said casing.

6. The apparatus of claim 5, wherein said ingress means is fluidly connected to said connector receptacle of said jet wash apparatus.

7. A method of jet washing of an ultrasonic streaming current detector, comprising the following steps:
 a. providing a cross-shaped tubular member having cross-member and longitudinal elements communicating with each other and further with a test fluid containing charge influencing species;
 b. providing a piston receiving member mounted coaxially with said longitudinal element;
 c. providing a casing substantially surrounding said piston receiving member;
 d. providing a pair of electrodes, the first of which is disclosed adjacent to a bottom end of said piston receiving member and the second of which is disposed in said piston receiving member above the first electrode;
 e. providing a reciprocating element mounted in the central bore of said piston receiving member;
 f. providing means for reciprocating said reciprocating element within the bore of said piston receiving member, so as to cause a continuous repetitive flow of said test fluid to and from said bore to thereby generate electrical signals across said electrodes;
 g. providing a means for amplifying said electrical signals generated across said electrodes, and means for utilizing said amplified signals;
 h. providing means for conducting said electrical signals generated across said electrodes from said electrodes to said means for amplifying said electrical signals and said means for utilizing said amplified signals;
 i. providing means for synchronizing said conduction of said electrical signals with the action of said reciprocating element;
 j. providing an ultrasonic cleaning device disposed adjacent to said piston receiving member and said casing for generating mechanical vibrations to prevent an agglomeration of said charge influencing species contained by said test fluid in the area about said electrodes;
 k. providing the jet wash apparatus with a connector receptacle connected in fluid communication with the bottom of said longitudinal element of said cross-shaped tubular member; with a cleaning fluid inlet means connector in fluid communication to the bottom of said connector receptacle, said cleaning fluid inlet means having an adjustable valve; with a conduit connected in fluid communication at its bottom end to said cleaning fluid inlet means and fluidly communicating with said piston receiving member at its top end;
 l. injecting a stream of said cleaning fluid through said cleaning fluid inlet;
 m. adjusting the flow rate of said stream of cleaning fluid by means of adjusting said adjustable valve;
 n. introducing said stream of cleaning fluid through said conduit and through said dielectric cap, thereby causing said cleaning fluid to be forcibly injected against said piston receiving member, said reciprocating element, and said casing, inter alia, thereby causing any undesirable charged particulate buildup thereon to be forcibly expelled through said apertures provided diametically opposite each other through said casing, and therethrough said reservoir of said cross-member element and through said egree means, thereby ensuring the generation of accurate results of said ultrasonic streaming current detector.

8. The method of operation of the apparatus of claim 7, whenever the condition occurs that said charge-influencing species contained by said test fluid agglomerates in the area about said electrodes of said ultrasonic streaming current detector, comprising the following steps:
 a. injecting a stream of said cleaning fluid through said cleaning fluid inlet;
 b. adjusting the flow rate of said stream of cleaning fluid by means of adjusting said adjustable valve;
 c. introducing said stream of cleaning fluid through said conduit and through said dielectric cap, thereby causing said cleaning fluid to be forcibly injected against said piston receiving member, said reciprocating element, and said casing, inter alia, thereby causing any undesirable charged particulate buildup thereon to be forcibly expelled through said apertures provided diametrically opposite each other through said casing, and therethrough said reservoir of said cross-member element and through said egress means, thereby ensuring the generation of accurate results by said ultrasonic streaming current detector.

9. The apparatus of claim 7, wherein said cleaning fluid comprises sodium hypochlorite.

10. The apparatus of claim 9, wherein said cleaing fluid comprises distilled water.

11. The apparatus of claim 11, wherein said conduit is made of polyethylene, and said piston receiving member and said reciprocating element are made of a dielectric material.

* * * * *